United States Patent [19]
Kashimoto et al.

[11] Patent Number: 5,856,303
[45] Date of Patent: Jan. 5, 1999

[54] PEPTIDE, A BRONCHUS-EXPANDING AGENT, AND A BLOOD-FLOW-IMPROVING AGENT

[75] Inventors: Kazuhisa Kashimoto; Yumiko Nagano, both of Ibaraki, Japan

[73] Assignee: Itoham Foods, Inc., Kobe, Japan

[21] Appl. No.: 776,815

[22] PCT Filed: Jun. 6, 1996

[86] PCT No.: PCT/JP96/01543

§ 371 Date: Feb. 7, 1997

§ 102(e) Date: Feb. 7, 1997

[87] PCT Pub. No.: WO96/41814

PCT Pub. Date: Dec. 27, 1996

[30] Foreign Application Priority Data

Jun. 9, 1995 [JP] Japan .................................. 7-143581
Oct. 2, 1995 [JP] Japan .................................. 7-255370

[51] Int. Cl.$^6$ .............................. A61K 38/00; C07K 5/00; C07K 7/00
[52] U.S. Cl. ............................... 514/12; 530/324
[58] Field of Search ................. 530/324; 514/12

[56] References Cited

U.S. PATENT DOCUMENTS

| | | | |
|---|---|---|---|
| 4,605,641 | 8/1986 | Bolin et al. | 514/12 |
| 4,734,400 | 3/1988 | Bolin et al. | 514/12 |

FOREIGN PATENT DOCUMENTS

| | | | |
|---|---|---|---|
| 0241926 | 10/1987 | European Pat. Off. | C07K 7/10 |
| 0463450 | 1/1992 | European Pat. Off. | C07K 7/10 |
| 62-246595 | 10/1987 | Japan . | |
| 4-297498 | 10/1992 | Japan . | |
| 06092991 | 4/1994 | Japan . | |

OTHER PUBLICATIONS

A. Miyata et al., Biochemical & Biophysical Research Communications, vol. 164, No. 1, pp. 567–574 (1989).
"Polypeptide with Broad Biological Activity: Isolation from Small Intestine", Science, vol. 169, pp. 1217–1218 (1970).
R.B. Merrifield, Synthesis of a Tetrapeptide, vol. 85, pp. 2149–2154 (1963).
Chemical Abstracts, vol. 122, p. 1111, No. 291534r, 1995.

Primary Examiner—Avis M. Davenport
Attorney, Agent, or Firm—Chapman and Cutler

[57] ABSTRACT

The present invention relates to a peptide represented by the general formula (1):

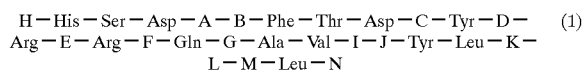

wherein A is Ala or Gly; B is Ile or Val; C is Asn or Ser; D is Thr or Ser; E is Leu or Tyr; each of F, I and J is Lys or Arg, and at least one of F, I and J is Arg; G is Met, Leu or Nle; K is Asn or Ala; L is Ser or Ala; M is Ile or Val; and N is —NH$_2$ or Asn—NH$_2$, excluding the combination where A is Ala, B is Val, C is Asn, D is Thr, E is Leu, K is Asn, L is Ser, M is Ile, and N is Asn—NH$_2$, and pharmaceutically acceptable salts thereof, as well as to a bronchus-expanding agent or a blood-flow-improving agent comprising said peptide or a pharmaceutically acceptable salt thereof as an active ingredient.

29 Claims, 4 Drawing Sheets

FIG.1

Relaxation Action of PACAP

FIG.2

Relaxation Action of Example 5

FIG.3

Relaxation Action of VIP

FIG.4

Relaxation Action of Example 11

PEPTIDE, A BRONCHUS-EXPANDING AGENT, AND A BLOOD-FLOW-IMPROVING AGENT

This application is a 371 of PCT/JP96/01543 filed Jun. 6, 1996.

FIELD OF THE INVENTION

The present invention relates to a novel peptide, a bronchus-expanding agent and a blood-flow-improving agent.

BACKGROUND OF THE INVENTION

VIP (vasoactive intestinal peptide) is one kind of physiologically active peptide called brain-gut peptide, the action of which is to promote blood flow and depress blood pressure. VIP was extracted from the intestine of a pig in 1970 and it consists of 28 amino acid residues (S. I. Said, V. Mutt Science, 169, 1217 (1970)).

PACAP (pituitary adenylate cyclase activating polypeptide) was isolated from the hypothalamus of a sheep in 1989 in a bioassay system using as an indicator the activation of adenylate cyclase from cultured pituitary cells, and it is a structurally determined peptide consisting of 38 amino acid residues (A. Miyata, A. Arimura et al., Biochem. Biophys. Res. Commun.,164, 567 (1989)). 27 amino acid residues from the N-terminal side of PACAP has the PACAP activity and the amino acid sequence of said 27 amino acids has a considerably similar structure to that of VIP.

VIP and PACAP are similar in amino acid sequence to secretin, glucagon etc. and are thus classified as peptides belonging to the glucagon family. By virtue of their strong action on vessel expansion and blood-flow promotion, VIP and PACAP are expected for use in the treatment of an ulcer, frostbite, bedsore, impotence etc. and in the restoration and growth of hair. In addition, VIP and PACAP have considerably strong relaxation action on the bronchial smooth muscle in the respiratory system, thus alleviating the smooth muscle contraction induced by stimulators such as acetylcholine, histamine, serotonin etc. Such relaxation action of VIP and PACAP differ from the relaxation action caused via adrenalin $\beta_2$ receptor by general bronchial expansion, so VIP and PACAP are expected to have an treatment effect on asthmatic spasm difficult to cure on which a stimulator of $\beta_2$ receptor does not effectively act.

Besides VIP and PACAP, a peptide consisting of 28 to 31 amino acid residues with bronchus expanding action, blood-pressure reducing action and hair restoring action is known (see Japanese Patent Application Laid-Open Publication Nos. 246,595/87, 83,012/89 and 297,498/92).

It is however desired to develop a bronchus-expanding agent and a blood-flow-improving agent superior to VIP, PACAP and other peptides in the durability of bronchus-expanding action and blood-flow increasing action.

DISCLOSURE OF THE INVENTION

The object of the present invention is to provide a novel peptide excellent in the durability of bronchus-expanding action and further excellent in blood-flow increasing action, a bronchus-expanding agent and a blood-flow-improving agent comprising said peptide as an active ingredient.

The present invention provides a peptide represented by the general formula (1):

wherein A is Ala or Gly; B is Ile or Val; C is Asn or Ser; D is Thr or Ser; E is Leu or Tyr; each of F, I and J is Lys or Arg, and at least one of F, I and J is Arg; G is Met, Leu or nLeu; K is Asn or Ala; L is Ser or Ala; M is Ile or Val; and N is —$NH_2$ or Asn—$NH_2$, excluding the combination where A is Ala, B is Val, C is Asn, D is Thr, E is Leu, K is Asn, L is Ser, M is Ile, and N is Asn—$NH_2$, or the general formula (2):

wherein A, B, C, D, E, F, G, I, J, K, L and M possess the same meanings defined as above; at least one of F, I and J is Arg; P is Asn or a chemical bond; Q is Lys, Arg, Lys-Arg, Arg—Arg or a chemical bond; and R is —OH or —$NH_2$, or pharmaceutically acceptable salts thereof.

Further, the present invention provides a bronchus-expanding agent comprising said peptide or a pharmaceutically acceptable salt thereof as an active ingredient.

Further, the present invention provides a blood-flow-improving agent comprising said peptide or a pharmaceutically acceptable salt thereof as an active ingredient.

Further, the present invention provides a pharmaceutical composition comprising said peptide or a pharmaceutically acceptable salt thereof and a pharmaceutically acceptable carrier.

Further, the present invention provides a method of expanding a bronchus, which comprises administrating an effective amount of said peptide or a pharmaceutically acceptable salt thereof into humans.

Further, the present invention provides a method of improving a blood flow, which comprises administrating an effective amount of said peptide or a pharmaceutically acceptable salt thereof into humans.

Further, the present invention provides use of said peptide or a pharmaceutically acceptable salt thereof for expanding a bronchus.

Further, the present invention provides use of said peptide or pharmaceutically acceptable salt thereof for improving a blood flow.

The peptide of the invention or a salt thereof is excellent in the durability of bronchus-expanding action resulting from the relaxation action of smooth muscle. Hence, the peptide of the invention and a salt thereof is useful as a bronchus-expanding agent.

In addition, the peptide of the invention or a salt thereof is excellent in blood-flow-increasing action and in its durability. Therefore, the peptide of the invention or a salt thereof is also useful as a blood-flow-improving agent and it can exert an improvement effect on a blood flow at a low dosage.

The abbreviations of amino acids, peptides, protective groups, solvents etc., in the present specification follow those according to International Union of Pure and Applied Chemistry (IUPAC) or International Union of Biochemistry (IUB) or conventional abbreviations in this field. Examples are shown below. If there can be optical isomers for amino acids etc., L-isomers are meant unless otherwise specified.

| | | |
|---|---|---|
| His: histidine residue | Ser: serine residue | Asp: aspartic acid residue |
| Ala: alanine residue | Val: valine residue | Phe: phenylalanine residue |

| | | |
|---|---|---|
| Thr: threonine residue | Tyr: tyrosine residue | Asn: asparagine residue |
| Leu: leucine residue | Arg: arginine residue | Lys: lysine residue |
| Gln: glutamine residue | Met: methionine residue | Ile: isoleucine residue |
| Gly: glycine residue | Nle: norleucine residue | |
| Boc: t-butyloxycarbonyl group | | Aoc: t-amyloxycarbonyl group |
| Bzl: benzyl group | | Z: benzyloxycarbonyl group |
| Tos: p-toluenesulfonyl group | | OBut: t-butylester |
| OMe: methylester | | OBz: benzylester |
| ONP: p-nitrophenylester | | Bom: benzyloxymethyl group |
| TFA: trifluoroacetic acid | | THF: tetrahydrofuran |
| DCM: dichloromethane | | DMF: dimethylforamide |
| DCC: dicyclohexylcarbodiimide | | |
| WSC: N-ethyl-N'-dimethylamino-propyl-carbodimimide | | |
| OSu: N-hydroxysuccinimide ester | | |
| HOSu: N-hydroxysuccinimide | | |
| HOBt: 1-hydroxybenzotriazole | | |
| DIEA: dissopropylethylamine. | | |

The peptides represented by the above formula (1) or (2) can be produced by conventional means for synthesis of known peptides. For example, these peptides can be produced in e.g. an azide method, acid chloride method, acid anhydride method, mixed acid anhydrides method, DCC method, active ester method (p-nitrophenylester method, N-hydroxysuccinic acid imide ester method, cyanomethylester method etc.), a method using Woodward reagent K, carboimidazole method, oxidation-reduction method, DCC-additive (HONB, HOBt, HOSu) method etc. according to methods described in e.g. "The Peptides" Vol. 1 (1966) [Schreder and Luhke: Academic Press, New York, U.S.A.] or "Peputido Gosei" (Peptide Synthesis) [Izumiya et al., Maruzen K. K. (1975), Japan]. These methods can be applied to both solid-phase synthesis and liquid-phase synthesis. According to the above-described methods for synthesis of conventional polypeptides, a target peptide can be produced in a stepwise elongation method where each of the amino acids in said peptide is linked sequentially to the C-terminal amino acid or in a fragment condensation method where partial fragments in said peptide are synthesized and then coupled to one another.

For example, the solid-phase synthesis in the stepwise elongation method can be carried out in accordance with the method of Merrifield, R. B. (Solid Phase Peptide Synthesis, J. Amer. Chem. Soc.,85, 2149–2159 (1963)) as follows: The C-terminal amino acid of a target peptide (that is, in the present invention, the amino acid sequence of the above general formula (1) or (2)) is protected on its amino group and then coupled to insoluble resin having functional groups capable of binding to carboxyl groups. The amino group is then deprotected, and to this free amino group is bound the next amino acid with its amino group protected. These steps are repeated many times, thus elongating the amino acid chain until the histidine residue at the 1-position of the formula (1) or (2). The peptide thus obtained is then cleaved off from the resin.

The above method requires the protection (that is, linking a protective group to the amino group) and the deprotection (that is, releasing the protective group from the amino group) for the amino group participating in peptide bonding between amino acids as well as the activation of the carboxyl group participating in peptide bonding between amino acids. If necessary, a protective group is further linked to a functional group in a side chain of the amino acid.

The protective group used in protecting the amino group includes those conventionally used. Examples are benzyloxycarbonyl (Z), t-butyloxycarbonyl (Boc), t-amyloxycarbonyl (Aoc), isobornyloxycarbonyl, p-methoxybenzyloxycarbonyl, 2-chloro-benzyloxycarbonyl, amadantyloxycarbonyl, trifluoroacetyl, phthaloyl, formyl, o-nitrophenylsulphenyl, and diphenylphosphinothioyl.

The protective group used in protecting the carboxyl group includes those conventionally used. Examples are alkyl esters such as methyl ester, ethyl ester, propyl ester, butyl ester and tert-butyl ester, benzyl ester, p-nitrobenzyl ester, methylbenzyl ester, p-chlorobenzyl ester, benzhydryl ester, benzyloxycarbonylhydrazide, tert-butyloxycarbonylhydrazide and tritylhydrazide.

The activation of the carboxyl group participating in peptide bonding can be carried out in any of the conventionally known methods described above, and the reagents etc. used in the activation can be selected from known ones. The activation of the carboxyl group involves reacting various reagents with said carboxyl group to form e.g. their corresponding acid chlorides, acid anhydrides or mixed acid anhydrides, azides, and active esters (for example, esters such as pentachlorophenol, p-nitrophenol, N-hydroxysuccinimide, N-hydroxybenztriazole, N-hydroy-5-norbornen-2,3-dicarboxyimide etc.).

For the amino acid with a functional group in its side chain, the functional group is preferably protected during the reaction of forming a peptide bond. In particular, His, Tyr, Thr, Lys, Asp, Arg and Ser are preferably protected at the functional group in their side chain. The protection of the functional group is carried out by linking the protective group to it in a conventional method. After the completion of peptide synthesis, the protective group is released.

The protective group used in protecting the imino group in His includes e.g. benzyloxymethyl (Bom), tosyl (Tos), benzyl (Bzl), benzyloxycarbonyl (z) and trityl.

The hydroxyl group in Ser and Thr can be protected by esterification or etherification, but its protection is not necessarily required. The protective group to be introduced by esterification includes e.g. lower alkanoyl groups such as acetyl etc., aroyl groups such as benzoyl etc., and carbonic acid-derived groups such as benzoyloxycarbonyl, ethyloxycarbonyl etc. Preferable examples of protective groups introduced by etherification are benzyl (Bzl), tetrahydropyranyl and tert-butyl.

The protective group used in protecting the hydroxyl group in Tyr includes e.g. benzyl (Bzl), bromobenzyloxycarbonyl (BrZ), dichlorobenzyl (Cl$_2$-Bzl), benzyloxycarbonyl (z), acetyl, and tosyl (Tos).

The protective group used in protecting the amino group in Lys includes e.g. benzyloxycarbonyl (Z), chlorobenzyloxycarbonyl (Cl-Z), dichlorobenzyl (Cl$_2$-Bzl), t-butyloxycarbonyl (Boc), and tosyl (Tos).

The protective group used in protecting the guanidino group in Arg includes e.g. tosyl (Tos), nitro, benzyloxycarbonyl (z), and t-amyloxycarbonyl (Aoc).

The protection of the carboxyl group in Asp is carried out by esterification with e.g. benzyl alcohol, methanol, ethanol or tert-butanol.

The reaction of forming a peptide bond can sometimes be carried out in the presence of a condensation reagent e.g. a carbodiimide reagent such as dicyclohexylcarbodiimide (DCC), carbodiimidazole etc., or tetraethyl pyrophosphate, benzotriazole-N-hydroxytrisdimethylaminophosphonium hexafluorophosphate (Bop reagent).

The insoluble resin used in the above solid-phase synthesis may be any resin having functional groups capable of binding to carboxyl groups. Examples are benzhydrylamine resin (BHA resin), chloromethyl resin, oxymethyl resin, aminomethyl resin, p-methylbenzhydrylamine resin (MBHA resin), 4-aminomethylphenoxymethyl resin, 4-hydroxymethylphenoxymethyl resin, 4-oxymethylphenylacetamidem ethyl resin (PAM resin) etc. The linking of the amino acid to the resin and cleavage of the synthesized peptide from the resin can be carried out in any of the conventionally known methods.

The solvent used in the above solid-phase synthesis may be any solvents known to be usable in forming a peptide bond, and examples are water-free or water-containing dimethylformamide (DMF), dimethyl sulfoxide (DMSO), pyridine, chloroform, dioxane, dichloromethane (DCM), tetrahydrofuran (THF), ethyl acetate, N-methylpyrrolidone, and hexamethyl phosphate triamide (HMPA). These solvents can be used singly or in combination.

The peptide thus prepared can be desalted and purified in a usual manner. For example, it can be desalted and purified by ion-exchange chromatography on DEAE-cellulose etc., partition chromatography on Sephadex LH-20, Sephadex G-25 etc., normal phase chromatography on silica gel etc., reverse phase chromatography on ODS-silica gel etc., or in high performance liquid chromatography (HPLC), etc.

The pharmaceutically acceptable salts of the peptides represented by the above formula (1) or (2) include e.g. acetate, hydrochloride, phosphate etc.

The peptide of the invention and salts thereof are useful as a bronchus-expanding agent by virtue of their bronchus-expanding action. Hence, the bronchus-expanding agent containing the peptide of the invention or a salt thereof as an active ingredient is useful in suppression and improvement of asthma etc.

As the bronchus-expanding agent, the peptide of the invention or a salt thereof can be administered as such, but usually it is mixed in a usual manner with various pharmaceutically acceptable carriers to be formed into preparations in the form of liquid, gel or solid, for oral or parenteral purposes. The administration method includes inhalation (e.g. with an aerosol agent), injection, application etc.

The dosage of the present peptide or a salt thereof when used as a bronchus-expanding agent is preferably in the range of about 1 ng/kg to 1 mg/kg (body weight)/day/person, although the dosage is determined depending on the purpose for use, symptom, the age and body weight etc. of a patient, method of administration, etc.

Further, the peptide of the invention or a salt thereof is excellent in blood-flow increasing action which is superior in durability. Hence, a blood-flow improving agent comprising the peptide of the invention or a salt thereof is effective for treatment of an ulcer, frostbite, bedsore, impotence etc. as well as for restoration and growth of hair.

The peptide of the invention or a salt thereof when used as a blood-flow improving agent is mixed with a conventional pharmaceutically acceptable carrier to be formed into pharmaceutical preparations, preferably in the form of an injection.

For preparation of such an injection, the resulting preparation is preferably sterilized and isotonic relative to blood. Any conventionally used diluents can be used for manufacture of a preparation in the form of an injection. Example of diluents are water, physiological saline etc. In this case, a sufficient amount of common salt or glycerin to prepare an isotonic solution can be contained in a preparation in the form of an injection. This preparation can contain a conventional buffer, soothing agent, preservative etc. and if necessary a coloring agent, preservative, flavoring agent, sweetener, etc., as well as other pharmaceuticals. The above active ingredient for injection purposes can be dissolved before use in distilled water. The method of administering the resulting pharmaceutical preparation is varied depending on the form of the preparation. For example, the preparation in the form of an injection is intravenously administered singly or after being mixed with conventional complements such as amino acids etc.

The present peptide or a salt thereof when used as a blood-flow-improving agent is administered preferably in 2 to 4 portions daily in the range of about 1 ng/kg to 1 mg/kg (body weight)/day/person, although the dosage is determined depending on the purpose for use, symptom conditions, etc.

BEST EMBODIMENTS FOR CARRYING OUT THE INVENTION

Hereinafter, the present invention is described in detail by reference to Examples, which however are not intended to limit the scope of the present invention.

In the following examples, the identification of the resulting purified peptide was carried out by measurement of retention time in high performance liquid chromatography (HPLC), measurement of degree of optical rotation, and amino acid analysis, as shown below.

High performance liquid chromatography (HPLC)

For analysis in high performance liquid chromatography, LC-Module-1 (Waters Ltd. Japan) was used.
(Analysis conditions in HPLC)
  Column : TSK Gel ODS-120T (4.6×250 mm)
  Solvent: 0.1% TFA-acetonitrile (linear gradient of from 20% to 50% acetonitrile for 30 min).
  Flow rate: 1 ml/min.
  Detection wavelength: 220 nm.
Degree of optical rotation
  For measurement of degree of optical rotation, DIC-370 (Nippon Bunko Kogyo K. K., Japan) was used.
  (Conditions for measurement of degree of optical rotation)
  Light source: Na lamp, 589 nm.
  Temperature: 20° C.
  Layer length: 100 mm.
  Concentration: 1% (0.1M in acetic acid).
Amino acid analysis
  The amino acid analysis was carried out by hydrolyzing a peptide at 110° C. for 20 hours in 6N HCl containing 0.1% phenol and analyzing the hydrolysate in Hitachi Amino Acid Analyzer L-8500 (Hitachi, Ltd., Japan).

EXAMPLE 1

Production of peptide 1

The solid-phase synthesizer used was Peptide Synthesizer 9600 (Milligen Bioresearch). Peptide 1 shown in SEQ ID NO:1 whose C-terminal group was amidated was produced by the following solid-phase synthesis and purification.

First, 694 mg MBHA resin (0.72 mmol/g amino group, manufactured by Peptide Kenkyuzyo K. K., Japan) was introduced into a reactor for peptide solid-phase synthesis and treated with 8 ml DCM (4 times, 1 minute each), 8 ml DCM containing 60% TFA (20 minutes), 4 ml DCM (3 times, 15 seconds each), 3 ml DMF solution containing 1 ml DIEA (2 times, 1 minute each), and 8 ml DMF (6 times, 40 seconds each) in this order with stirring in an argon stream. After each treatment, filtration was carried out.

Separately, 2 mmol amino-group-protected amino acid Boc-Leu—OH corresponding to the amino acid residue at the 27-position in SEQ ID NO:1 was dissolved in 4 ml DCM. This solution was introduced into a vessel for amino acid activation, and after 3 ml DCC (0.5M in DCM) and 4 ml HOBt (0.5M in DCM) were added to it, and they were reacted for 30 minutes. Thereafter, the reaction solution was filtered off and the filtrate was transferred to a concentration vessel. 3 ml DMF was added to it and the DCM was distilled off in an argon stream. Then, 3 ml DMF was added to the concentrate, and it was transferred to the above reactor for peptide solid-phase synthesis and reacted for 30 minutes. Then, the reaction mixture was washed with 8 ml DCM (6 times, 20 seconds each). Separately, 2 mmol Boc-Leu—OH was dissolved in 4 ml DCM and the solution was introduced into the reactor for amino acid activation and the same procedure as described above was repeated (double-coupling) and filtered. Boc-Leu-MBHA resin was thus obtained.

Then, the Boc-Leu-MBHA resin was washed with 8 ml DCM (4 times, 1 minute each) and filtered. This resin was treated with 8 ml DCM containing 60% TFA (20 minutes), 4 ml DCM (3 times, 15 seconds each) , 3 ml DMF solution containing 1 ml DIEA (2 times, 1 minute each), and 8 ml DMF (6 times, 40 seconds each) in this order with stirring in an argon stream. After each treatment, filtration was carried out.

Separately, 2 mmol amino-group-protected amino acid Boc-Val—OH corresponding to the amino acid residue at the 26-position in SEQ ID NO:1 was dissolved in 4 ml DCM and introduced into a vessel for amino acid activation, and after 1.5 ml DCC (0.5M in DCM) was added to it, and they were reacted for 7 minutes. Thereafter, the reaction solution was filtered off and the filtrate was transferred to a concentration vessel. 3 ml DMF was added to it and the DCM was distilled off in an argon stream. Then, 3 ml DMF was added to the concentrate, and it was transferred to the above reactor for peptide solid-phase synthesis and reaction was carried out for 30 minutes. Then, the reaction mixture was washed with 8 ml DCM (6 times, 20 seconds each) and filtered. Boc-Val-Leu-MBHA resin was thus obtained.

Then, the following amino-group-protected amino acids, corresponding to the 25th to 1st amino acids in SEQ ID NO:1 respectively, were coupled successively to it.

| Amino Acid No. | Protected Amino Acid | Amount (mmol) |
|---|---|---|
| 25 | Boc-Ala-OH | 2 |
| 24 | Boc-Ala-OH | 2 × 2 |
| 23 | Boc-Leu-OH | 2 |
| 22 | Boc-Tyr(Bzl)-OH | 2 |
| 21 | Boc-Arg(Tos)-OH | 2 × 2 |
| 20 | Boc-Arg(Tos)-OH | 2 × 2 |
| 19 | Boc-Val-OH | 2 |

-continued

| Amino Acid No. | Protected Amino Acid | Amount (mmol) |
|---|---|---|
| 18 | Boc-Ala-OH | 2 |
| 17 | Boc-Leu-OH | 2 |
| 16 | Boc-Gln-OH | 2 × 2 |
| 15 | Boc-Arg(Tos)-OH | 2 × 2 |
| 14 | Boc-Arg(Tos)-OH | 2 × 2 |
| 13 | Boc-Tyr(Bzl)-OH | 2 |
| 12 | Boc-Arg(Tos)-OH | 2 × 2 |
| 11 | Boc-Ser(Bzl)OH | 2 |
| 10 | Boc-Tyr(Bzl)-OH | 2 |
| 9 | Boc-Ser(Bzl)-OH | 2 |
| 8 | Boc-Asp(OBz)-OH | 2 |
| 7 | Boc-Thr(Bzl)-OH | 2 |
| 6 | Boc-Phe-OH | 2 |
| 5 | Boc-Ile-OH | 2 |
| 4 | Boc-Gly-OH | 2 |
| 3 | Boc-Asp(OBz)-OH | 2 |
| 2 | Boc-Ser(Bzl)-OH | 2 |
| 1 | Boc-His(Bom)-OH | 2 × 2 |

In the above solid-phase synthesis, double coupling was carried out in the case of Asn, Arg, Gln and His.

2.76 g of the following protected peptide-HBHA resin was thus obtained:

Boc-His(Bom)-Ser(Bzl)-Asp(OBz)-Gly-Ile-Phe-Thr(Bzl) -Asp(OBz)-Ser(Bzl)-Tyr (Bzl)-Ser(Bzl)-Arg(Tos)-Tyr(Bzl)- Arg(Tos)-Arg(Tos)-Gln-Leu-Ala-Val-Arg (Tos)-Arg(Tos)- Tyr(Bzl)-Leu-Ala-Ala-Val-Leu-MBHA resin.

5 ml anisole was added to 2.76 g of the above protected peptide-MBHA resin, and 25 ml anhydrous hydrogen fluoride was added to it and the mixture was reacted with stirring at 0° C. for 1 hour. Thereafter, the anhydrous hydrogen fluoride was distilled off under reduced pressure. The residue was washed with ether and then the peptide was extracted from it with 100 ml of 0.1M acetic acid.

The extract was stirred for 15 minutes together with 20 ml anion-exhange resin Amberlite IR-410 and the insoluble resin was removed by filtration. The suspension thus obtained was filtered through 0.22$\mu$ Millipore filter and the filtrate was lyophilized. 823 mg white powder was thus obtained. Then, this sample was applied to a column of CM-cellulose (2.5×30 cm) and eluted with a linear gradient of from 0.05M to 0.5M AcONH$_4$ (pH 7.0), and fraction Nos. 69 to 82 (10 ml/fraction) were combined and gave 382 mg of the desired peptide in partially purified form. This peptide was further purified in preparative high performance liquid chromatography.

Column: TSK Gel ODS-120T (21.5×300 mm).

Solvent: 0.1% TFA-acetonitrile (linear gradient of from 20% to 40% acetonitrile).

Flow rate: 10 ml/min.

The eluate corresponding to a peak of peptide 1 as the desired substance was lyophilized. The peptide in purified form was obtained in said HPLC in an amount of 63 mg per 100 mg of the partially purified peptide. The purified peptide 1 was determined for retention time in HPLC and for degree of optical rotation, and its amino acids were analyzed. The results are shown below:

Retention time in HPLC: 27.2 min.

$[\alpha]_D$: −55.8°

Amino acid analysis:

Asp(2) 2.17, Thr(1) 0.98, Ser(3) 2.45, Glu(1) 1.09, Gly(1) 1.03, Ala(3) 3.18, Val(2) 2.14, Ile(1) 0.96, Leu(3) 3.07, Tyr(3) 2.73, Phe(1) 0.92, His(1) 1.12, Arg(5) 5.16.

EXAMPLE 2

Peptide 2 shown in SEQ ID NO:2 whose C-terminal carboxyl group was amidated was obtained in purified form in the same manner as in Example 1. The yield of this purified peptide is shown below. Its retention time in HPLC and its degree of optical rotation were determined, and its amino acids were analyzed. The results are shown below:
Yield: 73 mg
Retention time in HPLC: 27.6 min.
$[\alpha]_D$: −53.2°
Amino acid analysis:
 Asp(2) 2.10, Thr(1) 0.97, Ser(3) 2.46, Glu(1) 0.97, Gly(2) 1.97, Ala(3) 3.15, Val(2) 2.13, Ile(1) 1.00, Leu(3) 3.08, Tyr(3) 2.75, Phe(1) 0.98, His(1) 0.99, Arg(5) 4.54.

EXAMPLE 3

Peptide 3 shown in SEQ ID NO:3 whose C-terminal carboxyl group was amidated was obtained in purified form in the same manner as in Example 1. The yield of this purified peptide is shown below. Its retention time in HPLC and its degree of optical rotation were determined, and its amino acids were analyzed. The results are shown below:
Yield: 88 mg
Retention time in HPLC: 27.0 min.
$[\alpha]_D$: −52.8°
Amino acid analysis:
 Asp(2) 2.11, Thr(1) 0.95, Ser(3) 2.56, Glu(1) 0.97, Gly(2) 2.00, Ala(3) 3.15, Val(2) 2.10, Ile(1) 1.00, Leu(3) 3.08, Tyr(3) 2.75, Phe(1) 0.98, His(1) 1.03, Arg(5) 5.14, Lys(1) 1.01.

EXAMPLE 4

Peptide 4 shown in SEQ ID NO:4 whose C-terminal carboxyl group was amidated was obtained in purified form in the same manner as in Example 1. The yield of this purified peptide is shown below. Its retention time in HPLC and its degree of optical rotation were determined, and its amino acids were analyzed. The results are shown below:
Yield: 84 mg
Retention time in HPLC: 25.1 min.
$[\alpha]_D$: −54.3°
Amino acid analysis:
 Asp(2) 2.09, Thr(1) 0.96, Ser(3) 2.44, Glu(1) 0.97, Gly(2) 2.01, Ala(3) 3.11, Val(2) 2.03, Ile(1) 1.02, Leu(3) 3.08, Tyr(3) 2.74, Phe(1) 0.97, His(1) 1.05, Arg(6) 6.10

EXAMPLE 5

Peptide 5 shown in SEQ ID NO:5 whose C-terminal carboxyl group was amidated was obtained in purified form in the same manner as in Example 1. The yield of this purified peptide is shown below. Its retention time in HPLC and its degree of optical rotation were determined, and its amino acids were analyzed. The results are shown below:
Yield: 76 mg
Retention time in HPLC: 24.4 min.
$[\alpha]_D$: −52.2°
Amino acid analysis:
 Asp(2) 2.11, Thr(1) 0.96, Ser(3) 2.47, Glu(1) 1.01, Gly(2) 2.00, Ala(3) 3.03, Val(2) 2.03, Ile(1) 1.02, Leu(3) 3.03, Tyr(3) 2.70, Phe(1) 0.97, His(1) 1.07, Arg(6) 6.15, Lys(1) 1.02.

EXAMPLE 6

Peptide 6 shown in SEQ ID NO:6 whose C-terminal carboxyl group was amidated was obtained in purified form in the same manner as in Example 1. The yield of this purified peptide is shown below. Its retention time in HPLC and its degree of optical rotation were determined, and its amino acids were analyzed. The results are shown below:
Yield: 85 mg
Retention time in HPLC: 23.6 min.
$[\alpha]_D$: −53.7°
Amino acid analysis:
 Asp(2) 2.09, Thr(1) 0.94, Ser(3) 2.51, Glu(1) 1.05, Gly(2) 2.00, Ala(3) 3.03, Val(2) 2.01, Ile(1) 1.02, Leu(3) 3.03, Tyr(3) 2.77, Phe(1) 0.97, His(1) 1.07, Arg(7) 7.11.

EXAMPLE 7

Peptide 7 shown in SEQ ID NO:7 was obtained in purified form in the same manner as in Example 1 except that 704 mg of Boc-Arg (Tos)-PAM resin (0.68 mmol/g amino group, produced by Peptide Kenkyuzyo K. K.), i.e. a resin having the C-terminal amino acid residue of the target peptide, was used. The yield of this purified peptide is shown below. Its retention time in HPLC and its degree of optical rotation were determined, and its amino acids were analyzed. The results are shown below:
Yield: 84 mg
Retention time in HPLC: 23.8 min.
$[\alpha]_D$: −56.7°
Amino acid analysis:
 Asp(2) 2.12, Thr(1) 0.96, Ser(3) 2.47, Glu(1) 1.01, Gly(2) 2.00, Ala(3) 3.03, Val(2) 2.03, Ile(1) 1.02, Leu(3) 3.03, Tyr(3) 2.70, Phe(1) 0.97, His(1) 1.03, Arg(6) 6.10, Lys(1) 1.02.

EXAMPLE 8

Peptide 8 shown in SEQ ID NO:8 whose C-terminal carboxyl group was amidated was obtained in purified form in the same manner as in Example 1. The yield of this purified peptide is shown below. Its retention time in HPLC and its degree of optical rotation were determined, and its amino acids were analyzed. The results are shown below:
Yield: 68 mg
Retention time in HPLC: 26.9 min.
$[\alpha]_D$: −58.7°
Amino acid analysis:
 Asp(5) 5.11, Thr(2) 1.72, Ser(2) 1.61, Glu(1) 1.10, Ala(2) 2.00, Val(2) 2.00, Ile(1) 1.02, Leu(4) 4.15, Tyr(2) 1.86, Phe(1) 0.99, His(1) 0.95, Arg(5) 4.75.

EXAMPLE 9

Peptide 9 shown in SEQ ID NO:9 whose C-terminal carboxyl group was amidated was obtained in purified form in the same manner as in Example 1. The yield of this purified peptide is shown below. Its retention time in HPLC and its degree of optical rotation were determined, and its amino acids were analyzed. The results are shown below:
Yield: 76 mg
Retention time in HPLC: 25.4 min.
$[\alpha]_D$: −52.9°
Amino acid analysis:
 Asp(5) 5.11, Thr(2) 1.83, Ser(2) 1.49, Glu(1) 1.09, Gly(1) 1.04, Ala(2) 2.01, Val(2) 2.01, Ile(1) 0.96, Leu(4) 4.19, Tyr(2) 2.03, Phe(1) 1.01, His(1) 1.07, Arg(6) 6.10, Lys(1) 1.05.

EXAMPLE 10

Peptide 10 shown in SEQ ID NO:10 whose C-terminal carboxyl group was amidated was obtained in purified form in the same manner as in Example 1. The yield of this purified peptide is shown below. Its retention time in HPLC and its degree of optical rotation were determined, and its amino acids were analyzed. The results are shown below:
Yield: 77 mg
Retention time in HPLC: 24.9 min.
$[\alpha]_D$: −52.5°
Amino acid analysis:
Asp(5) 5.12, Thr(2) 1.83, Ser(2) 1.55, Glu(1) 1.08, Gly(1) 1.03, Ala(2) 2.01, Val(2) 2.01, Ile(1) 0.96, Leu(4) 4.17, Tyr(2) 2.03, Phe(1) 1.01, His(1) 1.03, Arg(6) 6.15.

EXAMPLE 11

Peptide 11 shown in SEQ ID NO:11 whose C-terminal carboxyl group was amidated was obtained in purified form in the same manner as in Example 1. The yield of this purified peptide is shown below. Its retention time in HPLC and its degree of optical rotation were determined, and its amino acids were analyzed. The results are shown below:
Yield: 87 mg
Retention time in HPLC: 23.5 min.
$[\alpha]_D$: −55.5°
Amino acid analysis:
Asp(5) 5.11, Thr(2) 1.83, Ser(2) 1.49, Glu(1) 1.09, Gly(1) 1.04, Ala(2) 2.01, Val(2) 2.01, Ile(1) 0.96, Leu(4) 4.19, Tyr(2) 2.03, Phe(1) 1.01, His(1) 1.07, Arg(6) 6.10, Lys(1) 1.05.

EXAMPLE 12

Peptide 12 shown in SEQ ID NO:12 whose C-terminal carboxyl group was amidated was obtained in purified form in the same manner as in Example 1. The yield of this purified peptide is shown below. Its retention time in HPLC and its degree of optical rotation were determined, and its amino acids were analyzed. The results are shown below:
Yield: 78 mg
Retention time in HPLC: 23.0 min.
$[\alpha]_D$: −56.2°
Amino acid analysis:
Asp(5) 5.13, Thr(2) 1.84, Ser(2) 1.49, Glu(1) 1.08, Gly(1) 1.03, Ala(2) 2.01, Val(2) 2.01, Ile(1) 0.96, Leu(4) 4.19, Tyr(2) 2.03, Phe(1) 1.01, His(1) 1.02, Arg(7) 7.11.

EXAMPLE 13

Peptide 13 shown in SEQ ID NO:13 was obtained in purified form in the same manner as in Example 1 except that 704 mg of Boc-Arg(Tos)-PAM resin, i.e. a resin having the C-terminal amino acid residue of the target peptide, was used. The yield of this purified peptide is shown below. Its retention time in HPLC and its degree of optical rotation were determined, and its amino acids were analyzed. The results are shown below:
Yield: 83 mg
Retention time in HPLC: 22.8 min.
$[\alpha]_D$: −58.6°
Amino acid analysis:
Asp(5) 5.15, Thr(2) 1.83, Ser(2) 1.53, Glu(1) 1.09, Gly(1) 1.01, Ala(2) 2.01, Val(2) 2.01, Ile(1) 1.02, Leu(4) 4.10, Tyr(2) 1.86, Phe(1) 1.00, His(1) 0.95, Arg(6) 6.15.

EXAMPLE 14

Peptide 14 shown in SEQ ID NO:14 whose C-terminal carboxyl group was amidated was obtained in purified form in the same manner as in Example 1. The yield of this purified peptide is shown below. Its retention time in HPLC and its degree of optical rotation were determined, and its amino acids were analyzed. The results are shown below:
Yield: 64 mg
Retention time in HPLC: 25.1 min.
$[\alpha]_D$: −52.7°
Amino acid analysis:
Asp(2) 2.17, Thr(1) 0.98, Ser(3) 2.55, Glu(1) 1.03, Gly(1) 1.03, Ala(3) 3.18, Met(1) 0.96, Val(2) 2.14, Ile(1) 0.96, Leu(2) 2.07, Tyr(3) 2.73, Phe(1) 1.00, His(1) 1.01, Arg(5) 5.15.

EXAMPLE 15

Peptide 15 shown in SEQ ID NO:15 whose C-terminal carboxyl group was amidated was obtained in purified form in the same manner as in Example 1. The yield of this purified peptide is shown below. Its retention time in HPLC and its degree of optical rotation were determined, and its amino acids were analyzed. The results are shown below:
Yield: 62 mg
Retention time in HPLC: 26.2 min.
$[\alpha]_D$: −52.5°
Amino acid analysis:
Asp(2) 2.11, Thr(1) 0.95, Ser(3) 2.45, Glu(1) 1.04, Gly(1) 1.03, Ala(3) 3.18, Val(2) 2.14, Ile(1) 0.96, Leu(2) 2.10, Tyr(3) 2.73, Phe(1) 0.96, His(1) 1.02, Arg(5) 5.16, nLeu(1) 1.02.

EXAMPLE 16

Purified peptides 1 to 15 obtained in Examples 1 to 15 were examined for their bronchus-expanding action in the following manner and compared with that of VIP and PACAP.

Male guinea pigs each weighing 450 to 500 g were cut at the jugular veins to open the chests, and immediately the tracheae were immediately removed. Their tracheae were immediately placed in a Krebs solution and cut into loops and then formed into a chain by linking the cartilage parts with one another via a steel string. Then, the cartilage parts in the opposite side to the smooth muscular parts were cut such that the smooth muscular parts were attached to one another. The resulting sample was placed in an about 10-ml isothermic organ bath and perpendicularly suspended. The lower part was fixed and the upper part was connected to a grass force transducer with a load of 1.4 g. A gas of 94% oxygen and 6% carbon dioxide was sufficiently blown into this sample while a Krebs solution containing $0.1\mu$ mol/l carbachol was dropped to it at a rate of 0.33 ml/min. to determine relaxation action. Because the relaxation reaction occurs depending on the content of a test sample in this drop solution, this can be used to compare the relaxation action of VIP and PACAP and that of the peptides of the invention on the bronchial smooth muscle.

A solution of each of VIA, PACAP and the peptides of the invention was prepared in a concentration as high as 100-fold than the final concentration so that its concentration in the organ bath could be adjusted. 30 minutes after the carbachol-containing Krebs solution was dropped, 100 $\mu$l of the sample solution was dropped.

It was assumed that the degree of contraction of the smooth muscle is 0 in the absence of carbachol and the degree is 100 in the presence of carbachol. Minimum contraction degree A (i.e. maximum relaxation value) in the presence of the sample was determined, and maximum relaxation degree B was calculated as follows:

Maximum relaxation degree B (%)=100−A

The time required to reach half of the maximum relaxation value (referred to hereinafter as "half-time T") after the addition of the sample was determined.

Figure 1:
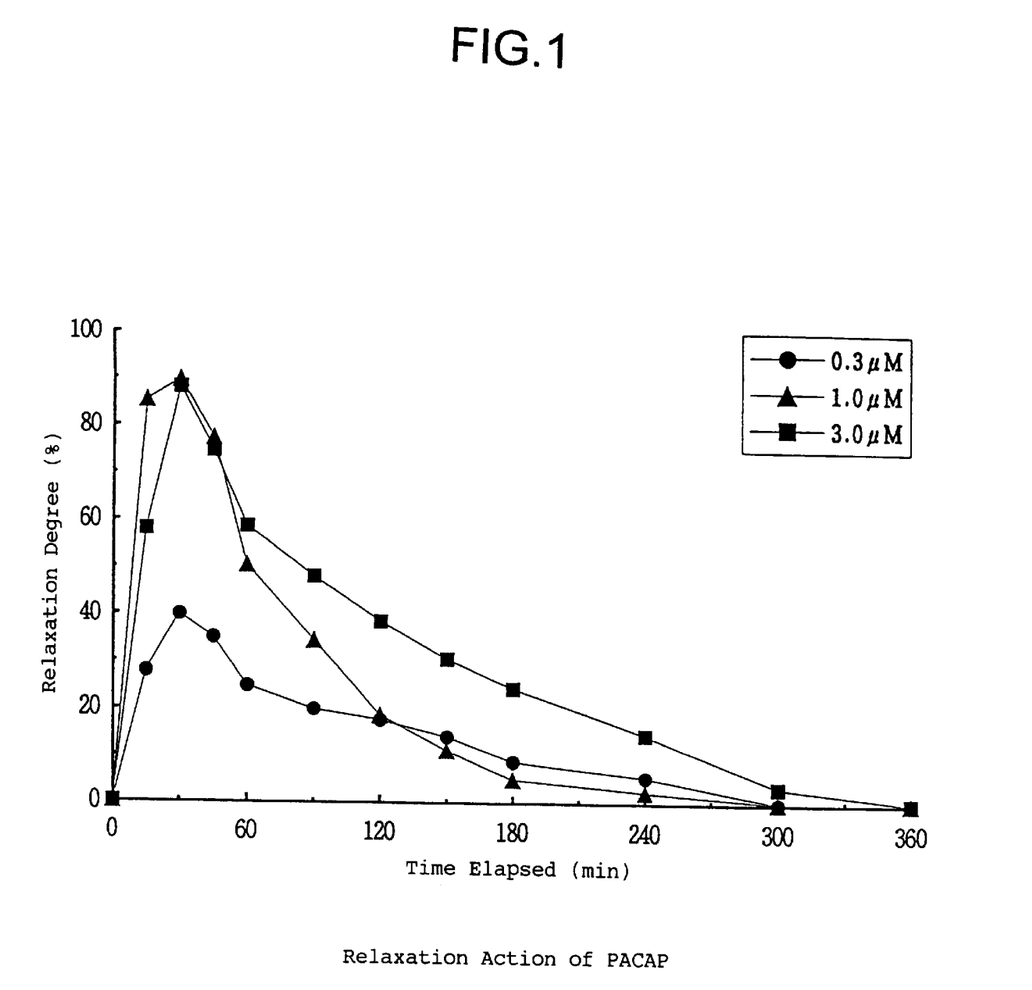
FIG. 1 is a graph showing a change with time in the degree of relaxation of bronchial smooth muscle in the case of administration of PACAP.
Figure 2:
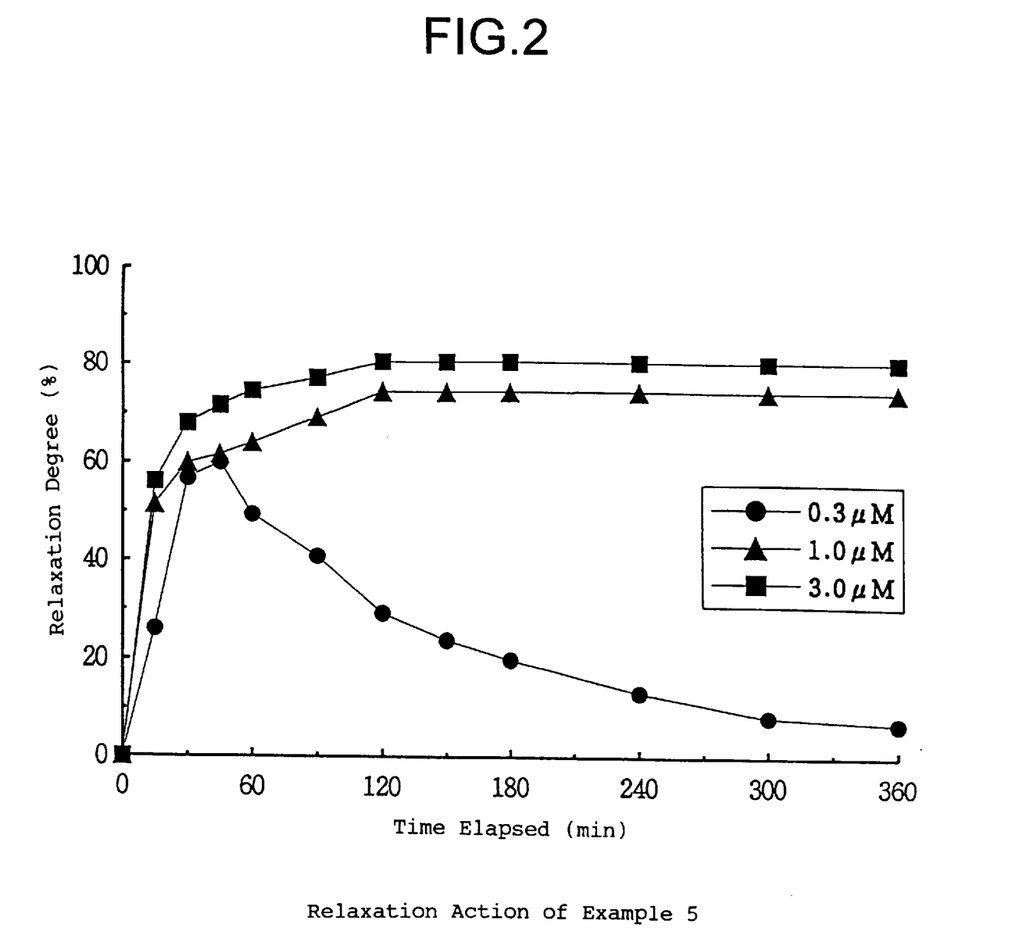
FIG. 2 is a graph showing a change with time in the degree of relaxation of bronchial smooth muscle in the case of administration of Peptide 5 shown in SEQ ID NO:5.
Figure 3:
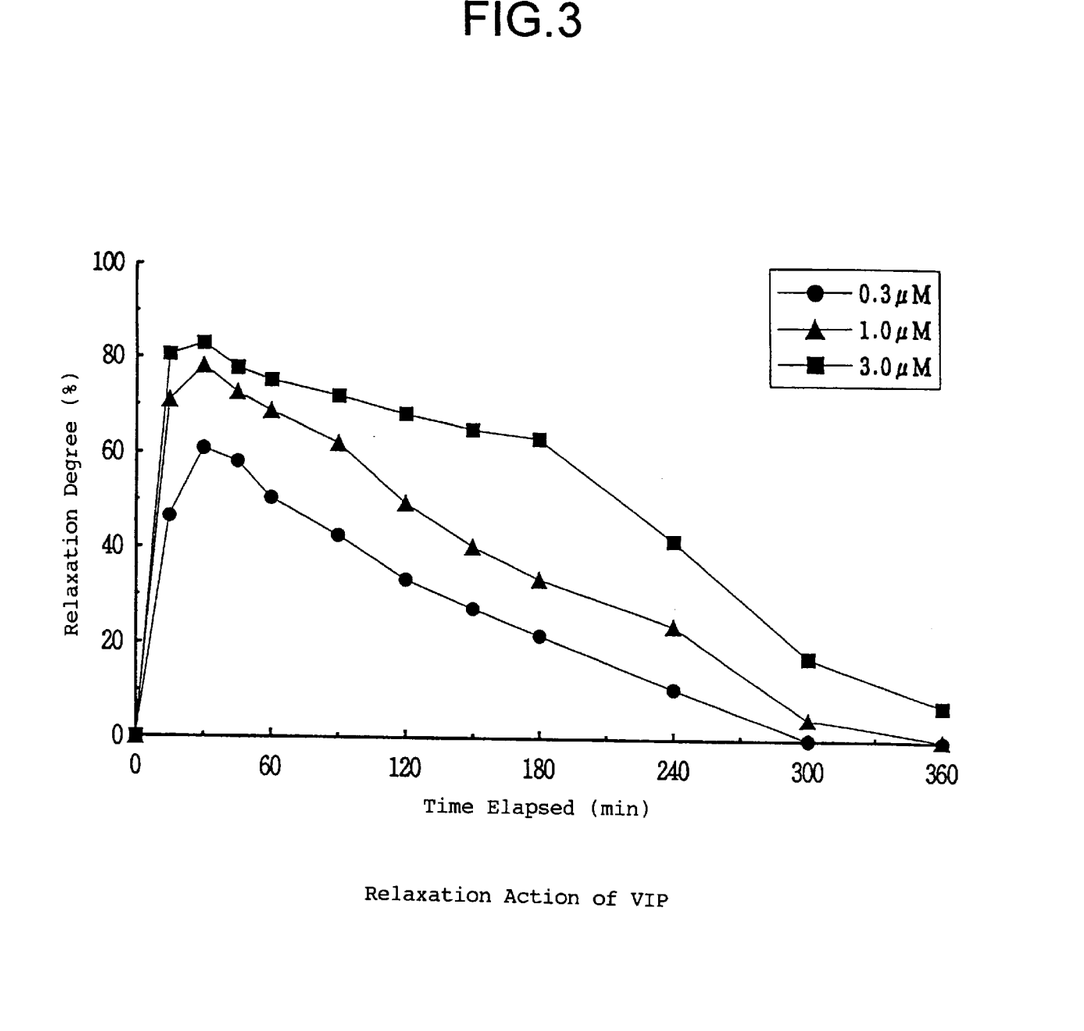
FIG. 3 is a graph showing a change with time in the degree of relaxation of bronchial smooth muscle in the case of administration of VIP.
Figure 4:
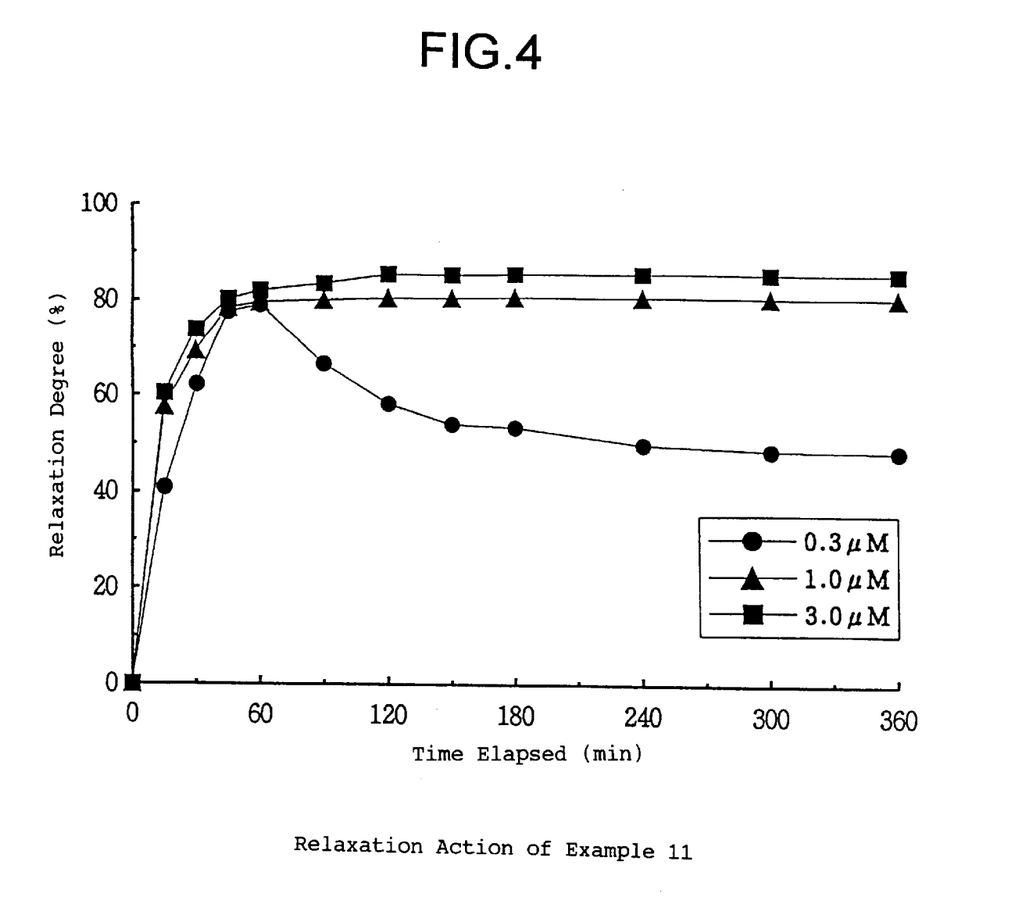
FIG. 4 is a graph showing a change with time in the degree of relaxation of bronchial smooth muscle in the case of administration of Peptide 11 shown in SEQ ID NO:11.

A change in the relaxation degree of the bronchial smooth muscle with time was determined using each peptide at 3 dosages of 0.3 μM, 1 μM, and 3 μM respectively. The results are shown in the drawings: PACAP in FIG. 1; peptide 5 obtained in Example 5, in FIG. 2; VIP in FIG. 3; and peptide 11 obtained in Example 11, in FIG. 4. The maximum relaxation degree B at a dosage of 3 μM is 75% for peptide 5 and 80% for peptide 11, and half-time T is 360 minutes or more in both the cases. From these results, the peptides of the invention, while possessing a similar relaxation effect to those of VIP and PACAP, exhibit superior durability, i.e. a longer working period than those of VIP and PACAP.

Table 1 shows maximum relaxation degree B and half-life T for each peptide at each dosage.

TABLE 1

|  | 0.3 μM | | 1 μM | | 3 μM | |
| --- | --- | --- | --- | --- | --- | --- |
|  | B (%) | T (min) | B (%) | T (min) | B (%) | T (min) |
| PACAP | 40 | 60 | 90 | 60 | 90 | 100 |
| VIP | 45 | 130 | 80 | 150 | 85 | 240 |
| Peptide 1 in Example 1 | 50 | 100 | 80 | 240 | 85 | >360 |
| Peptide 2 in Example 2 | 55 | 120 | 80 | 240 | 85 | >360 |
| Peptide 3 in Example 3 | 55 | 120 | 80 | 240 | 85 | >360 |
| Peptide 4 in Example 4 | 55 | 120 | 80 | 240 | 85 | >360 |
| Peptide 5 in Example 5 | 60 | 120 | 80 | >360 | 75 | >360 |
| Peptide 6 in Example 6 | 65 | 150 | 80 | >360 | 75 | >360 |
| Peptide 7 in Example 7 | 60 | 120 | 80 | >360 | 75 | >360 |
| Peptide 8 in Example 8 | 50 | 150 | 80 | 300 | 80 | >360 |
| Peptide 9 in Example 9 | 55 | 180 | 80 | 300 | 80 | >360 |
| Peptide 10 in Example 10 | 55 | 200 | 80 | 300 | 80 | >360 |
| Peptide 11 in Example 11 | 65 | 300 | 85 | >360 | 85 | >360 |
| Peptide 12 in Example 12 | 65 | 300 | 90 | >360 | 85 | >360 |
| Peptide 13 in Example 13 | 65 | 300 | 90 | >360 | 85 | >360 |
| Peptide 14 in Example 14 | 40 | 100 | 80 | 240 | 85 | >360 |
| Peptide 15 in Example 15 | 40 | 100 | 80 | 240 | 85 | >360 |

EXAMPLE 17

Purified peptides 1 to 15 obtained in Examples 1 to 15 were examined for their blood-flow increasing action and compared with those of VIP and PACAP.

Wistar male rats each weighing 220 to 250 g were anesthetized by intraperitoneal administration of pentobarbital (25 mg/kg) and fixed on their back. An arterial canula was inserted into the carotid and then connected to a blood-pressure transducer (DX-300, Nippon Koden, Japan) via a doom kit (SCK-512, Nippon Koden) filled with heparin-containing physiological saline (10 U/ml) to measure blood pressure with a strain blood-pressure amplifier (AP-601G, Nippon Koden). Further, a blood-flow measurement probe (FR-030T, Nippon Koden) was attached to the right femoral artery and then connected to an electromagnetic blood-flow meter (MFV-3200, Nippon Koden) to measure blood flow. The dosage of each peptide intraarterially administrated was 100 pmol/kg.

Table 2 shows an increase in blood flow in rats given each peptide.

TABLE 2

|  | Blood Flow (ml/min) |
| --- | --- |
| PACAP | 16.04 ± 5.92 |
| VIP | 10.18 ± 3.38 |
| Peptide 1 in Example 1 | 50.02 ± 42.34 |
| Peptide 2 in Example 2 | 52.63 ± 39.58 |
| Peptide 3 in Example 3 | 52.13 ± 37.85 |
| Peptide 4 in Example 4 | 51.87 ± 37.24 |
| Peptide 5 in Example 5 | 54.60 ± 41.05 |
| Peptide 6 in Example 6 | 53.71 ± 46.46 |
| Peptide 7 in Example 7 | 55.05 ± 46.71 |
| Peptide 8 in Example 8 | 53.75 ± 37.31 |
| Peptide 9 in Example 9 | 54.26 ± 35.95 |
| Peptide 10 in Example 10 | 55.86 ± 34.69 |
| Peptide 11 in Example 11 | 57.04 ± 38.67 |
| Peptide 12 in Example 12 | 57.34 ± 41.88 |
| Peptide 13 in Example 13 | 56.76 ± 36.15 |
| Peptide 14 in Example 14 | 52.92 ± 32.12 |
| Peptide 15 in Example 15 | 52.63 ± 31.05 |

No particular change was observed in the blood pressure of rats given 100 pmol/kg of each of peptides 1 to 15.

EXAMPLE 18

Acute Toxicity Test

Peptides 1 to 15 obtained in Examples 1 to 15 were dissolved in physiological saline and administered intravenously into mice at a dosage of 10 mg/kg. The result indicated that every mouse survived.

What is claimed is:

1. A peptide represented by the formula (1):

H—His—Ser—Asp—Gly—B—Phe—Thr—Asp—C—Tyr—D—  (1)
Arg—E—Arg—F—Gln—G—Ala—Val—I—J—Tyr—Leu—K—
L—M—Leu—N—O—P wherein B and M are Ile or Val; C is Asn or Ser; D is Thr or Ser; E is Leu or Tyr; each of F, I and J is Lys or Arg, and at least one of them is Arg; G is selected from the group consisting of Leu, Met, and Nle; K is Ala or Asn; L is Ala or Ser; N is Asn or a chemical bond; O is selected from the group consisting of Lys, Arg and the chemical bond; and P is selected from the group consisting of Arg—NH$_2$, Arg—OH, and —NH$_2$.

2. A peptide of claim 1 represented by the formula (2):

H—His—Ser—Asp—Gly—Ile—Phe—Thr—Asp—Ser—Tyr—  (2)
Ser—Arg—Tyr—Arg—F—Gln—G—Ala—Val—I—J—Tyr—Leu—
Ala—Ala—Val—Leu—N—O—P wherein G, I, J, N to P are the same as those of claim 1.

3. A peptide of claim 2 represented by the following formula (3):

H—His—Ser—Asp—Gly—Ile—Phe—Thr—Asp—Ser—Tyr—  (3)
Ser—Arg—Tyr—Arg—Arg—Gln—Leu—Ala—Val—Arg—Arg—
Tyr—Leu—Ala—Ala—Val—Leu—NH$_2$.

4. A peptide of claim 2 represented by the following formula (4):

H—His—Ser—Asp—Gly—Ile—Phe—Thr—Asp—Ser—Tyr—  (4)
Ser—Arg—Tyr—Arg—Arg—Gln—Leu—Ala—Val—Arg—Arg—
Tyr—Leu—Ala—Ala—Val—Leu—Gly—NH$_2$.

5. A peptide of claim 2 represented by the following formula (5):

H—His—Ser—Asp—Gly—Ile—Phe—Thr—Asp—Ser—Tyr—  (5)
Ser—Arg—Tyr—Arg—Arg—Gln—Leu—Ala—Val—Arg—Arg—
Tyr—Leu—Ala—Ala—Val—Leu—Gly—Lys—NH$_2$.

6. A peptide of claim 2 represented by the following formula (6):

H—His—Ser—Asp—Gly—Ile—Phe—Thr—Asp—Ser—Tyr—  (6)
Ser—Arg—Tyr—Arg—Arg—Gln—Leu—Ala—Val—Arg—Arg—
Tyr—Leu—Ala—Ala—Val—Leu—Gly—Arg—NH$_2$.

7. A peptide of claim 2 represented by the following formula (7):

H—His—Ser—Asp—Gly—Ile—Phe—Thr—Asp—Ser—Tyr—  (7)
Ser—Arg—Tyr—Arg—Arg—Gln—Leu—Ala—Val—Arg—Arg—
Tyr—Leu—Ala—Ala—Val—Leu—Gly—Lys—Arg—NH$_2$.

8. A peptide of claim 2 represented by the following formula (8):

H—His—Ser—Asp—Gly—Ile—Phe—Thr—Asp—Ser—Tyr—  (8)
Ser—Arg—Tyr—Arg—Arg—Gln—Leu—Ala—Val—Arg—Arg—
Tyr—Leu—Ala—Ala—Val—Leu—Gly—Arg—Arg—NH$_2$.

9. A peptide of claim 2 represented by the following formula (9):

H—His—Ser—Asp—Gly—Ile—Phe—Thr—Asp—Ser—Tyr—  (9)
Ser—Arg—Tyr—Arg—Arg—Gln—Leu—Ala—Val—Arg—Arg—
Tyr—Leu—Ala—Ala—Val—Leu—Gly—Lys—Arg—OH.

10. A peptide of claim 2 represented by the following formula (10):

H—His—Ser—Asp—Gly—Ile—Phe—Thr—Asp—Ser—Tyr—  (10)
Ser—Arg—Tyr—Arg—Arg—Gln—Met—Ala—Val—Arg—
Arg—Tyr—Leu—Ala—Ala—Val—Leu—NH$_2$.

11. A peptide of claim 2 represented by the following formula (11):

H—His—Ser—Asp—Gly—Ale—Phe—Thr—Asp—Ser—Tyr—  (11)
Ser—Arg—Tyr—Arg—Arg—Gln—Nle—Ala—Val—Arg—
Arg—Tyr—Leu—Ala—Ala—Val—Leu—NH$_2$

12. A peptide represented by the general formula (12):

H—His—Ser—Asp—Ala—B—Phe—Thr—Asp—C—Tyr—  (12)
D—Arg—E—Arg—F—Gln—G—Ala—Val—I—J—Tyr—Leu—
K—L—M—Leu—N—O—P—Q wherein B and M are Ile or Val; C is Asn or Ser; D is Thr or Ser; E is Leu or Tyr; each of F, I and J is Lys or Arg, and at least one of them is Arg; G is selected from the group consisting of Leu, Met, and Nle; K is Ala or Asn; L is Ala or Ser; N is Asn or a chemical bond; O is Gly or the chemical bond; P is selected from the group consisting of Lys, Arg, and the chemical bond; Q is selected from the group consisting of Arg—NH$_2$, Arg—OH and —NH$_2$; excluding the peptide wherein B is Val, C is Asn, D is Thr, E is Leu, K is Asn, L is Ser, and M is Ile.

13. A peptide of claim 12 represented by the general formula (13):

H—His—Ser—Asp—Ala—Val—Phe—Thr—Asp—Ser—Tyr—  (13)
Thr—Arg—Leu—Arg—F—Gln—Leu—Ala—Val—I—J—Tyr—
Leu—Asn—Ser—Ile—Leu—Asn—Gly—P—Q wherein F, I, J, P and Q are the same as those of claim 12.

14. A peptide of claim 13 represented by the following formula (14):

H—His—Ser—Asp—Ala—Val—Phe—Thr—Asp—Ser—Tyr—  (14)
Thr—Arg—Leu—Arg—Arg—Gln—Leu—Ala—Val—Arg—
Arg—Tyr—Leu—Asn—Ser—Ile—Leu—Asn—Gly —NH$_2$

15. A peptide of claim 13 represented by the following formula (15):

H—His—Ser—Asp—Ala—Val—Phe—Thr—Asp—Ser—Tyr—  (15)
Thr—Arg—Leu—Arg—Arg—Gln—Leu—Ala—Val—Arg—
Arg—Tyr—Leu—Asn—Ser—Ile—Leu—Asn—Gly —Lys—NH$_2$

16. A peptide of claim 13 represented by the following formula (16):

H—His—Ser—Asp—Ala—Val—Phe—Thr—Asp—Ser—Tyr—  (16)
Thr—Arg—Leu—Arg—Arg—Gln—Leu—Ala—Val—Arg—
Arg—Tyr—Leu—Asn—Ser—Ile—Leu—Asn—Gly —Arg—NH$_2$

17. A peptide of claim 13 represented by the following formula (17):

H—His—Ser—Asp—Ala—Val—Phe—Thr—Asp—Ser—Tyr—  (17)
Thr—Arg—Leu—Arg—Arg—Gln—Leu—Ala—Val—Arg—
Arg—Tyr—Leu—Asn—Ser—Ile—Leu—Asn—Gly —Lys—
Arg—NH$_2$

18. A peptide of claim 13 represented by the following formula (18):

H—His—Ser—Asp—Ala—Val—Phe—Thr—Asp—Ser—Tyr—  (18)
Thr—Arg—Leu—Arg—Arg—Gln—Leu—Ala—Val—Arg—
Arg—Tyr—Leu—Asn—Ser—Ile—Leu—Asn—Gly —Lys—
Arg—OH

19. A peptide of claim 13 represented by the following formula (19):

H—His—Ser—Asp—Ala—Val—Phe—Thr—Asp—Ser—Tyr—  (19)
Thr—Arg—Leu—Arg—Arg—Gln—Leu—Ala—Val—Arg—
Arg—Tyr—Leu—Asn—Ser—Ile—Leu—Asn—Gly —Arg—
Arg—NH$_2$

20. A pharmaceutical composition comprising the peptide according to claim 1, or a pharmaceutically acceptable salt thereof as an active ingredient.

21. A bronchodilator comprising the peptide according to claim 1, or a pharmaceutically acceptable salt of the peptide thereof as an active ingredient.

22. A vasodilator comprising the peptide according to claim 1, or a pharmaceutically acceptable salt thereof as an active ingredient.

23. A method for treating a disease caused by bronchoconstriction comprising administrating an effective amount of peptide of claim 1, or a pharmaceutically acceptable salt thereof.

24. A method for treating a disease caused vasoconstriction by comprising administrating an effective amount of peptide of claim 1, or a pharmaceutically acceptable salt thereof.

25. A pharmaceutical composition comprising the peptide according to claim 12, or a pharmaceutically acceptable salt thereof as an active ingredient.

26. A bronchodilator comprising the peptide according to claim 12, or a pharmaceutically acceptable salt of the peptide thereof as an active ingredient.

27. A vasodilator comprising the peptide according to claim 20, or a pharmaceutically acceptable salt thereof as an active ingredient.

28. A method for treating a disease caused by bronchoconstriction comprising administrating an effective amount of peptide of claim 12, or a pharmaceutically acceptable salt thereof.

29. A method for treating a disease caused vasoconstriction by comprising administrating an effective amount of peptide of claim 12, or a pharmaceutically acceptable salt thereof.

* * * * *

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
( A ) LENGTH: 27 amino acids
( B ) TYPE: amino acid
( C ) STRANDEDNESS: unknown
( D ) TOPOLOGY: linear ( i i ) MOLECULE TYPE: peptide ( x i ) SEQUENCE DESCRIPTION: SEQ ID NO: 1:

His  Ser  Asp  Gly  Ile  Phe  Thr  Asp  Ser  Tyr  Ser  Arg  Tyr  Arg  Arg  Gln

```
            1               5                      10                     15

Leu  Ala  Val  Arg  Arg  Tyr  Leu  Ala  Ala  Val  Leu
                    20                       25
```

( 2 ) INFORMATION FOR SEQ ID NO: 2:

( i ) SEQUENCE CHARACTERISTICS:
        ( A ) LENGTH: 28 amino acids
        ( B ) TYPE: amino acid
        ( C ) STRANDEDNESS: unknown
        ( D ) TOPOLOGY: linear     ( i i ) MOLECULE TYPE: peptide     ( x i ) SEQUENCE DESCRIPTION: SEQ ID NO: 2:

```
His  Ser  Asp  Gly  Ile  Phe  Thr  Asp  Ser  Tyr  Ser  Arg  Tyr  Arg  Arg  Gln
 1               5                      10                           15

Leu  Ala  Val  Arg  Arg  Tyr  Leu  Ala  Ala  Val  Leu  Gly
                    20                       25
```

( 2 ) INFORMATION FOR SEQ ID NO: 3:

( i ) SEQUENCE CHARACTERISTICS:
        ( A ) LENGTH: 29 amino acids
        ( B ) TYPE: amino acid
        ( C ) STRANDEDNESS: unknown
        ( D ) TOPOLOGY: linear     ( i i ) MOLECULE TYPE: peptide     ( x i ) SEQUENCE DESCRIPTION: SEQ ID NO: 3:

```
His  Ser  Asp  Gly  Ile  Phe  Thr  Asp  Ser  Tyr  Ser  Arg  Tyr  Arg  Arg  Gln
 1               5                      10                           15

Leu  Ala  Val  Arg  Arg  Tyr  Leu  Ala  Ala  Val  Leu  Gly  Lys
                    20                       25
```

( 2 ) INFORMATION FOR SEQ ID NO: 4:

( i ) SEQUENCE CHARACTERISTICS:
        ( A ) LENGTH: 29 amino acids
        ( B ) TYPE: amino acid
        ( C ) STRANDEDNESS: unknown
        ( D ) TOPOLOGY: linear     ( i i ) MOLECULE TYPE: peptide     ( x i ) SEQUENCE DESCRIPTION: SEQ ID NO: 4:

```
His  Ser  Asp  Gly  Ile  Phe  Thr  Asp  Ser  Tyr  Ser  Arg  Tyr  Arg  Arg  Gln
 1               5                      10                           15

Leu  Ala  Val  Arg  Arg  Tyr  Leu  Ala  Ala  Val  Leu  Gly  Arg
                    20                       25
```

( 2 ) INFORMATION FOR SEQ ID NO: 5:

( i ) SEQUENCE CHARACTERISTICS:
        ( A ) LENGTH: 30 amino acids
        ( B ) TYPE: amino acid
        ( C ) STRANDEDNESS: unknown
        ( D ) TOPOLOGY: linear     ( i i ) MOLECULE TYPE: peptide     ( x i ) SEQUENCE DESCRIPTION: SEQ ID NO: 5:

```
His  Ser  Asp  Gly  Ile  Phe  Thr  Asp  Ser  Tyr  Ser  Arg  Tyr  Arg  Arg  Gln
 1               5                      10                           15

Leu  Ala  Val  Arg  Arg  Tyr  Leu  Ala  Ala  Val  Leu  Gly  Lys  Arg
                    20                       25                    30
```

( 2 ) INFORMATION FOR SEQ ID NO: 6:

( i ) SEQUENCE CHARACTERISTICS:
        ( A ) LENGTH: 30 amino acids
        ( B ) TYPE: amino acid
        ( C ) STRANDEDNESS: unknown
        ( D ) TOPOLOGY: linear     ( i i ) MOLECULE TYPE: peptide     ( x i ) SEQUENCE DESCRIPTION: SEQ ID NO: 6:

```
His Ser Asp Gly Ile Phe Thr Asp Ser Tyr Ser Arg Tyr Arg Arg Gln
 1               5                  10                  15
Leu Ala Val Arg Arg Tyr Leu Ala Ala Val Leu Gly Arg Arg
            20                  25                  30
```

( 2 ) INFORMATION FOR SEQ ID NO: 7:

( i ) SEQUENCE CHARACTERISTICS:
        ( A ) LENGTH: 30 amino acids
        ( B ) TYPE: amino acid
        ( C ) STRANDEDNESS: unknown
        ( D ) TOPOLOGY: linear     ( i i ) MOLECULE TYPE: peptide     ( x i ) SEQUENCE DESCRIPTION: SEQ ID NO: 7:

```
His Ser Asp Gly Ile Phe Thr Asp Ser Tyr Ser Arg Tyr Arg Arg Gln
 1               5                  10                  15
Leu Ala Val Arg Arg Tyr Leu Ala Ala Val Leu Gly Lys Arg
            20                  25                  30
```

( 2 ) INFORMATION FOR SEQ ID NO: 8:

( i ) SEQUENCE CHARACTERISTICS:
        ( A ) LENGTH: 29 amino acids
        ( B ) TYPE: amino acid
        ( C ) STRANDEDNESS: unknown
        ( D ) TOPOLOGY: linear     ( i i ) MOLECULE TYPE: peptide     ( x i ) SEQUENCE DESCRIPTION: SEQ ID NO: 8:

```
His Ser Asp Ala Val Phe Thr Asp Asn Tyr Thr Arg Leu Arg Arg Gln
 1               5                  10                  15
Leu Ala Val Arg Arg Tyr Leu Asn Ser Ile Leu Asn Gly
            20                  25
```

( 2 ) INFORMATION FOR SEQ ID NO: 9:

( i ) SEQUENCE CHARACTERISTICS:
        ( A ) LENGTH: 30 amino acids
        ( B ) TYPE: amino acid
        ( C ) STRANDEDNESS: unknown
        ( D ) TOPOLOGY: linear     ( i i ) MOLECULE TYPE: peptide     ( x i ) SEQUENCE DESCRIPTION: SEQ ID NO: 9:

```
His Ser Asp Ala Val Phe Thr Asp Asn Tyr Thr Arg Leu Arg Arg Gln
 1               5                  10                  15
Leu Ala Val Arg Arg Tyr Leu Asn Ser Ile Leu Asn Gly Lys
            20                  25                  30
```

( 2 ) INFORMATION FOR SEQ ID NO: 10:

( i ) SEQUENCE CHARACTERISTICS:
  ( A ) LENGTH: 30 amino acids
  ( B ) TYPE: amino acid
  ( C ) STRANDEDNESS: unknown
  ( D ) TOPOLOGY: linear ( i i ) MOLECULE TYPE: peptide ( x i ) SEQUENCE DESCRIPTION: SEQ ID NO: 10:

His Ser Asp Ala Val Phe Thr Asp Asn Tyr Thr Arg Leu Arg Arg Gln
 1               5                  10                  15
Leu Ala Val Arg Arg Tyr Leu Asn Ser Ile Leu Asn Gly Arg
                20                  25                  30

( 2 ) INFORMATION FOR SEQ ID NO: 11:

( i ) SEQUENCE CHARACTERISTICS:
    ( A ) LENGTH: 31 amino acids
    ( B ) TYPE: amino acid
    ( C ) STRANDEDNESS: unknown
    ( D ) TOPOLOGY: linear ( i i ) MOLECULE TYPE: peptide ( x i ) SEQUENCE DESCRIPTION: SEQ ID NO: 11:

His Ser Asp Ala Val Phe Thr Asp Asn Tyr Thr Arg Leu Arg Arg Gln
 1               5                  10                  15
Leu Ala Val Arg Arg Tyr Leu Asn Ser Ile Leu Asn Gly Lys Arg
                20                  25                  30

( 2 ) INFORMATION FOR SEQ ID NO: 12:

( i ) SEQUENCE CHARACTERISTICS:
    ( A ) LENGTH: 31 amino acids
    ( B ) TYPE: amino acid
    ( C ) STRANDEDNESS: unknown
    ( D ) TOPOLOGY: linear ( i i ) MOLECULE TYPE: peptide ( x i ) SEQUENCE DESCRIPTION: SEQ ID NO: 12:

His Ser Asp Ala Val Phe Thr Asp Asn Tyr Thr Arg Leu Arg Arg Gln
 1               5                  10                  15
Leu Ala Val Arg Arg Tyr Leu Asn Ser Ile Leu Asn Gly Arg Arg
                20                  25                  30

( 2 ) INFORMATION FOR SEQ ID NO: 13:

( i ) SEQUENCE CHARACTERISTICS:
    ( A ) LENGTH: 31 amino acids
    ( B ) TYPE: amino acid
    ( C ) STRANDEDNESS: unknown
    ( D ) TOPOLOGY: linear ( i i ) MOLECULE TYPE: peptide ( x i ) SEQUENCE DESCRIPTION: SEQ ID NO: 13:

His Ser Asp Ala Val Phe Thr Asp Asn Tyr Thr Arg Leu Arg Arg Gln
 1               5                  10                  15
Leu Ala Val Arg Arg Tyr Leu Asn Ser Ile Leu Asn Gly Lys Arg
                20                  25                  30

( 2 ) INFORMATION FOR SEQ ID NO: 14:

( i ) SEQUENCE CHARACTERISTICS:
    ( A ) LENGTH: 27 amino acids
    ( B ) TYPE: amino acid
    ( C ) STRANDEDNESS: unknown -continued (D) TOPOLOGY: linear (ii) MOLECULE TYPE: peptide (xi) SEQUENCE DESCRIPTION: SEQ ID NO: 14:

His Ser Asp Gly Ile Phe Thr Asp Ser Tyr Ser Arg Tyr Arg Arg Gln
1               5                   10                  15
Met Ala Val Arg Arg Tyr Leu Ala Ala Val Leu
            20                  25

(2) INFORMATION FOR SEQ ID NO: 15:

(i) SEQUENCE CHARACTERISTICS:
(A) LENGTH: 27 amino acids
(B) TYPE: amino acid
(C) STRANDEDNESS: unknown
(D) TOPOLOGY: linear (ii) MOLECULE TYPE: peptide (ix) FEATURE:
(A) NAME/KEY: Norleucine (Nle)
(B) LOCATION: 17

(xi) SEQUENCE DESCRIPTION: SEQ ID NO: 15:

His Ser Asp Gly Ile Phe Thr Asp Ser Tyr Ser Arg Tyr Arg Arg Gln
1               5                   10                  15
Xaa Ala Val Arg Arg Tyr Leu Ala Ala Val Leu
            20                  25